(12) United States Patent
Everson

(10) Patent No.: US 10,154,705 B2
(45) Date of Patent: Dec. 18, 2018

(54) FOOT ORTHOTIC DESIGN SYSTEM

(75) Inventor: Dan Franklin Everson, Coolum Beach (AU)

(73) Assignee: Kinetic Orthotics Pty Ltd, Mudjumba, QLD (AU)

( * ) Notice: Subject to any disclaimer, the term of this patent is extended or adjusted under 35 U.S.C. 154(b) by 885 days.

(21) Appl. No.: 14/093,589

(22) PCT Filed: May 21, 2012

(86) PCT No.: PCT/AU2012/000562
§ 371 (c)(1),
(2), (4) Date: Dec. 2, 2013

(87) PCT Pub. No.: WO2012/162724
PCT Pub. Date: Dec. 6, 2012

(65) Prior Publication Data
US 2014/0316711 A1    Oct. 23, 2014

(30) Foreign Application Priority Data

Jun. 1, 2011    (AU) ................ 2011902135

(51) Int. Cl.
*A43D 1/02*    (2006.01)
*A61F 5/14*    (2006.01)
*A61B 5/107*    (2006.01)

(52) U.S. Cl.
CPC .............. *A43D 1/02* (2013.01); *A61B 5/1074* (2013.01); *A61F 5/14* (2013.01)

(58) Field of Classification Search
None
See application file for complete search history.

(56) References Cited

U.S. PATENT DOCUMENTS

| 7,069,665 | B1 | 7/2006 | Adriano | |
| 8,152,744 | B2 * | 4/2012 | Mukumoto | ............. A43B 7/28 600/587 |
| 2002/0048392 | A1 | 4/2002 | Kim | |
| 2008/0282580 | A1 | 11/2008 | Ji-Woog | |
| 2011/0083345 | A1 | 4/2011 | Santopietro | |

FOREIGN PATENT DOCUMENTS

| GB | 2370487 | 7/2002 |
| GB | 2370487 | 10/2004 |
| WO | 2005086857 | 9/2005 |
| WO | 2006068513 | 6/2006 |
| WO | 2006116642 | 11/2006 |

OTHER PUBLICATIONS

Lee et al, The Journal of Foot and Ankle Surgery, vol. 44, No. 2 Mar./Apr. 2005 p. 78-113.*
Karas et al. J Prosthet Orthot 2002 14:82-93.*

* cited by examiner

Primary Examiner — Joseph Woitach

(57) ABSTRACT

The invention relates to a system for the design of patient-specific orthotics, and particularly approaches the design of patient-specific orthotics upon an assessment of the patient's gait cycle. This enables the practitioner to precisely prescribe a kinetic orthotic that will optimize the way in which force is transferred during that patient's gait cycle.

8 Claims, 10 Drawing Sheets

FOOT ORTHOTIC DESIGN SYSTEM

CROSS-REFERENCE TO RELATED APPLICATION

This application claims the benefit of PCT Application Number PCT/AU2012/000562; filed May 21, 2012 and Australian Application No. 2011902135; filed Jun. 1, 2011 and incorporates by reference in its entirety the PCT and Australian Application into the current non-provisional application.

FIELD OF INVENTION

The present invention relates to a system for design of patient-specific orthotics. The invention particularly approaches the design of patient-specific orthotics upon an assessment of the patient's gait cycle which enables the practitioner to precisely prescribe a kinetic orthotic that will optimise the way in which force is transferred during that patient's gait cycle.

BACKGROUND OF THE INVENTION

Current orthotic design is largely unsystematic. Arbitrary applications of two-dimensional anatomical measurements have been shown to be unreliable, whatever their theoretical basis. A record of the foot contour alone is sometimes considered sufficient as the basis for orthotic design, but unless practitioners can take into account the balance of forces required for efficient locomotion, (i.e. kinetic data) they cannot accurately correct the condition of a patient.

Traditionally, orthotic manufacture takes place in two stages. The first stage, in the hands of the practitioner, is typically based on taking an impression so as to capture the foot shape, usually as a cast or model. The forefoot to rear-foot alignment in or around neutral position of the sub-talar joint is then assessed. The recorded foot shape is then modified in order to produce an improved (corrected) forefoot to rear-foot relationship. Following further clinical observations, other modifications to the cast can be made. For example the contour of the heel area and the shape of the medial and lateral longitudinal arches can be changed.

In the second stage of the process the orthotic manufacturer depends not only on the accuracy and adequacy of the prescription, but also on how accurately it can be translated for manufacture allowing for any inherent limitations of the method.

The most common problems with this process overall, whether the original design data are computer-generated or obtained manually, is the lack of consistency in both (i) how practitioners complete their evaluation and how orthotic manufacturers transform the data provided into a material orthotic product. This has led to a multitude of different approaches and a multitude of different outcomes.

Improving Current Practice the Kinetic Orthotic

Improving the efficiency of an individual's gait cycle should produce a lasting improvement in mobility and a decrease in any pathology related to biomechanical inefficiency. The design objective has been to create a "kinetic orthotic" by which muscular energy is most efficiently transferred in the gait cycle of a patient rather than an orthotic which merely compensates for abnormal foot topology, which is the functional limit of many designs.

Functioning Foot

In the functioning foot there are specific relationships between the anatomical structures commonly identified from both the frontal plane and the sagittal plane of reference. Instability can result from a misalignment between the forefoot and rear-foot which prevents the foot from functioning in a fully integrated manner. However such a simple structural (kinematic) classification as this overlooks the critical matter of how muscular energy is transmitted through anatomical structures in such a way as to confer normal motion (kinetic function) on the foot. For example, the pronation force about the sub-talor joint axis is known to increase as a result of structural misalignment. But an analysis in kinetic terms would account for the origin and magnitude of the pronation force and why this force affects the sub-talor joint. Once the problem is presented in kinetic terms, the anatomical structures are seen to play their part in the resolution and transmission of forces rather than suggesting their source.

Kinetic Processes in the Foot

Kinetic processes in the foot have been described by Kirby in terms of a dynamic equilibrium between the sum of pronation and supination forces occurring about the sub-talar joint axis. ("Rotational Equilibrium" theory (Kirby, K. A. 2001 "Sub-talar joint axis location and rotational equilibrium theory of foot function" JAPMA 91(9): 465-487)). Assessed from the sagittal plane of reference, the foot has been described as a compound pivot made up of three key pivots. The three key sagittal plane pivots can be named the "Heel rocker" the "Ankle Rocker" and the "Forefoot Rocker". Foot pronation results when a restriction occurs at either the ankle pivot or the forefoot pivot during gait. Restriction is revealed by the inability of the ankle or forefoot rocker to function normally. Restriction can be anatomical or physiological in origin and its extent can be influenced by footwear or orthotics or both. If restriction at a key pivot sites persists of foot becomes chronically unstable, pronation becomes endemic. This process can lead to deterioration in pivotal function and further instability.

In summary, pronation is frequently observed to follow restriction at a key pivot site (a structural feature). It is now understood that it is the changing distribution of mechanical forces as a result of the restriction and/or instability that actually brings about the condition of pronation.

BRIEF DESCRIPTION OF THE DRAWINGS

Representative embodiments of the present invention are herein described, by way of example only, with reference to the accompanying drawings.

DESCRIPTION OF THE INVENTION

Figure 1:
FIG. 1 illustrates the performance of a Kirby's test in accordance with a representative embodiment of the present invention.

Having regard to these insights, a diagnosis and a system for design of patient-specific orthotics has been developed focused principally on dealing with the kinetics of pronation rather than attempting to solve a formal problem in kinematics based on anatomical analysis. It has been observed that stabilisation and the facilitation of movement are inter-related. In particular, it is believed that the force that causes pronation is directly proportional to the force necessary to facilitate dynamic function at a key pivot site. When the pronatory force is extreme the effort needed to reduce the dynamic restriction is directly proportional to the reduction in the threshold force necessary to facilitate dynamic function at a key pivot site.

The invention is aimed at implementing this approach.

Accordingly, there is provided a method for the selection of an orthotic for a patient's foot comprising:
(a) subjecting the foot to one or more of the following tests and ascribing a test value(s) within a predetermined set of relative values for each test which is indicative of one or more properties of the patient's foot:
 (i) supination resistance test (as defined); and
 (ii) Jack's test (as defined);
(b) recording each test value in a database;
(c) comparing the test values to control values indicative of one or more predetermined orthotic designs stored in the database; and
(d) selecting an orthotic design(s) from the predetermined orthotic designs dependent on that comparison.

Using this approach, it is possible to satisfy orthotic design parameters with a high degree of accuracy. The design parameters themselves are individually prescribed according to a set of specific functional tests already widely documented in terms of inter-user reliability.

According to the method of the present invention, step (a) may further include one or more of a skeletal integrity test, a fascial chord tension test, an ankle joint stiffness-lunge test, a principal activity velocity test, a sagittal plane morphology test, and a hamstring stiffness test.

The invention provides two distinct advantages over existing methods, namely a high level of consistency and a reliable individualised design. It can provide calibrated performance data for research in this area, formerly impossible to obtain. Clinically, orthotics designed by this method lead to more effective treatment of the presenting symptoms and also lead to a distinctive improvement in overall mobility.

Mobility is a primary cause of concern to all health care insurance providers. It is well known that as people lose their mobility their health costs escalate. With globally aging populations, clinical intervention accurately targeted at improving mobility has the potential to reduce health costs of risks associated with a sedentary lifestyle such as heart disease and diabetes.

More explanation of the various tests is as follows:
(a) Supination Resistance Test—This is the amount of force required to resupinate the foot. With the patient standing in a relaxed weight bearing position, the force is graded on various levels and recorded from very low to very high. This index reveals where the centre of pressure is to be applied to the foot by the orthotic device, whether towards the back or the front. Foot integrity is also estimated from the amount of change in arch amplitude observed when the foot goes from a non-weight bearing position to a weight bearing. The change in arch amplitude may be measured within a range of five increments categorised from very low to very high; if the amplitude changes by two increments, the foot is classified as a foot with poor integrity, whereas if the change is just one increment the foot would be classified as one with good integrity. If there is no change then the integrity measure is scored as excellent. These integrity measures give further information for application of the design parameters that relates to the amount of rear foot to fore foot support. (See detailed description of the invention)
(b) Windlass mechanism test—Jack's Test and Fascial Chord Tension Test. The force required to lift the hallux when the patient's foot is in a full weight bearing position is determined by The Jacks Test. When the hallux is lifted, the foot automatically begins to resupinate. The force to initiate the foot resupination is graded on three levels form low to high. This index provides additional information as to the placement of the centre pressure in the orthotic design. Fascial Chord Tension Test is as follows. With the foot non-weight bearing, the first metatarsal is dorsi-flexed and the prominence of the fascial chord is recorded. The prominence of the fascial chord is graded from low to high. This parameter is important as this allows the design to be modified to accommodate the fascial chord by way of a fascial groove. It is important to be able to adjust the design this way to help protect and facilitate the windlass effect. The orthotic design may require further adjustment including wedging in the rear foot to help push the chord out of the way. (See detailed description of the invention)
(c) Sagittal plane morphology test. This categorises the foot in terms of the gradient, the anterior calcaneal surface and the foot apex position. The gradient is evaluated as low, medium, or high. The foot apex position when combined with the gradient is categorised as rear, central, or forward, providing key information on the amount of soft tissue that surrounds the anterior heel area and can affect the amount of rear foot orthotic contour applied in the design. (See detailed description of the invention)

(d) Hamstrings tension test. This is a test indicating the amount of tension in the hamstrings so as to determine the possible compensatory impact on the ankle joint in the close kinetic chain. Hamstring tension is graded on three levels low, medium and high. When the tension is categorised as high changes are made to the design so as to facilitate sagittal plane function. (See detailed description of the invention)

(e) Lunge test. Failure in this test implies that greater ankle joint facilitation must be provided for in the design. The design will reflect the increased force needed to establish foot resupination. (See detailed description of the invention)

(f) Principal activity velocity test. The principle activity velocity is defined as the level of activity the device is being designed for whether that is predominantly standing or moderate walking or running. The activity is graded on three levels from low to high. This is recorded as an index. When applied to the design it influences whether there is a need to more closely contour to the foot type or wedge more the rear foot area of the orthotic. The greater the velocity the greater the force of correction required and the further back the device apex should be.

DETAILED DESCRIPTION OF THE INVENTION

Diagnostic Criteria and Design Selection Tests
(1) Supination Resistance

Supination Resistance is widely used in clinical practice to determine how much force is needed to facilitate resupination of the foot about the sub-talar joint axis. Supination Resistance may be graded on five different levels from very low to very high.

The information shown in Table 1 below describes how the supination resistance test influences the selection of a basic design category (discussed later in this specification);

TABLE 1

| 01. | Very low/low sup resistance = | Kinetic extended heel |
| 02. | Low to moderate supination resistance = | Kinetic shell |
| 03. | Moderate supination resistance = | Kinetic control |
| 04. | Moderate to high supination resistance = | Kinetic rear control |
| 05. | High supination resistance = | Kinetic blake |
| 06. | High to very high supination resistance = | Kinetic ultra wedge |

The higher the level of resistance, the greater is the force that an orthotic must carry in order to assist with balancing foot function. Supination resistance affects the level of correction in two ways recognised by the system. Firstly the higher the supination resistance the further back you apex the curvature of the arch in the orthotic. Secondly the higher the supination resistance the greater the degree of correction is applied to the orthotic design. The supination resistance test has been tested for reliability. Four clinicians of differing levels of experience performed the test on 44 subjects (88 feet) on 2 separate days. The test had good reliability overall, with an inter-tester intra-class correlation coefficient of 0.89.

A commonly used test to assess supination resistance is the test described by Kirby (Kirby K A. "Sub-talar joint axis location and rotational equilibrium theory of foot function" JAPMA 91(9): 465-487. 2001).

(a) Kirby's Test

By way of illustration, and as shown in FIG. 1 of the drawings, the index and middle fingers are placed under the Sustentaculum Tali. Upward motion is applied, and the force required to initiate this motion is recorded. Details of this test are set out below in Table 2. This test was described and the relationship between the magnitude of force and the sub-talar joint axis position was related to the common goal of using an orthotic device to balance the respective forces.

TABLE 2

| Test | Description | Variable Range | Unit |
| --- | --- | --- | --- |
| Supination resistance test result | Arch being pulled in an upward direction by two fingers | Very low | 0-60 newtons |
| | | Low | 60-120 newtons |
| | | Medium | 121-160 newtons |
| | | High | 161 190 newtons |
| | | Very high | 191 to 270 newtons |

(b) Skeletal Integrity

Figure 2:
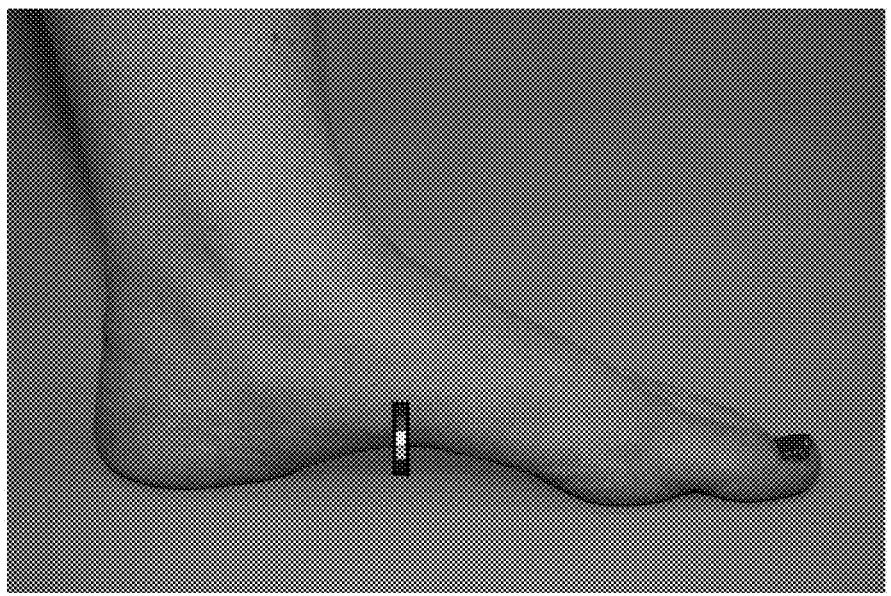
FIG. 2 illustrates the measurement of skeletal integrity in accordance with a representative embodiment of the present invention.

Skeletal integrity is the degree of changed observed in the foot contour from non-weight bearing to weight bearing, such as shown in FIG. 2 of the drawings. This observation is recorded in five different categories from very low to very high, as shown in Tables 3 and 4 below. The degree of change from non-weight-bearing to weight-bearing is compared to ascertain if the change exceeds one category. When the change exceeds one category, then the degree of skeletal integrity will influence how much contour the design will apply to the foot. When the integrity is high then the impact of contouring in the design is less important as the skeletal integrity and its ability to self-support is less of a problem.

TABLE 3

| Test | Description | Variable Range | Unit |
| --- | --- | --- | --- |
| Non weight bearing arch height | Medial long arch diagram/graphic, non-weight bearing | Very low | 0-10 mm |
| | | Low | 11-18 mm |
| | | Medium | 19-26 mm |
| | | High | 27-32 mm |
| | | Very high | 33-40 mm |

TABLE 4

| Test | Description | Variable Range | Unit |
| --- | --- | --- | --- |
| Weight bearing arch height | Medial long arch diagram/graphic, weight bearing | Very low | 0-10 mm |
| | | Low | 11-18 mm |
| | | Medium | 19-26 mm |
| | | High | 27-32 mm |
| | | Very high | 33-40 mm |

Results from observational tests relate to a "relative change" in foot position: Very High, High, Medium, Low, and Very Low (i.e. red to green)

A movement of more than two colours (i.e. from red to green) is considered significant.

The greater the change in arch the more the design has to reflect the non weight bearing contour.

(2) Windlass Mechanism Test

Figure 3:
FIGS. 3 and 4 illustrate the performance of a Jack's test in accordance with a representative embodiment of the present invention.
Figure 4:
Figure 5:
FIG. 5 illustrates the performance of a Fascial Chord test in accordance with a representative embodiment of the present invention.

This test comprises two sub tests, the Jack's Test as shown in FIGS. 3 and 4 of the drawings, and the Fascial Chord Test as shown in FIG. 5 of the drawings.

The information shown in Table 5 below describes how the outcome of the Jack's test correlates the other measure of supination resistance in influencing design selection of certain orthotic designs discussed later in this specification.

TABLE 5

| 01. | Low to moderate Jacks test = | Kinetic shell |
| --- | --- | --- |
| 02. | Moderate Jacks test = | Kinetic control |
| 03. | Moderate to high Jacks test = | Kinetic rear control |
| 04. | High Jacks Test = | Kinetic Blake/kinetic wedge |

The force required to lift the hallux when the foot is in a full weight bearing position is recorded. When the hallux is lifted the foot will automatically begin to resupinate imitating the Windlass Mechanism which is activated as the foot moves through the toe-off phase of the gait cycle. The Windlass Mechanism is characterised by the reflexive resupination of the foot triggered by the dorsi-flexion of the great toe. The higher the force, the greater the control required in the design. How this force is calibrated is displayed in Table 6 below.

Sensitivity and Specificity of the Functional Hallux Limitus Test to Predict Foot Function. Payne, C, Chuter, V, Miller, K. 2002. *J Am Podiatric Med Assoc*. Vol 92(5): 269-271

TABLE 6

| Test | Description | Variable Range | Force newtons |
| --- | --- | --- | --- |
| Jacks Test | Big toe joint goes through range of motion from flat on the floor up to about 45 degrees | Low (−ve) Medium High (+ve) | 0-100 101-200 201-300 >300 = dislocation |

It is also important to measure fascial chord tension. If this parameter is not accommodated for in the orthotic design the Windlass Mechanism could be disrupted. The Windlass Mechanism is the action that occurs when the foot moves through the toe-off phase of the gait cycle and is characterised by the reflexive resupination of the foot triggered by the dorsi-flexion of the great toe. The test is done with the foot non-weight-bearing; the first metatarsal is then dorsi-flexed. The amount by which the fascial chord is exposed is recorded. The tension is categorised in three levels; low, medium, and high, as shown in Table 7 below.

TABLE 7

| 1 | Fascial chord tension low = | No need for fascial accommodation |
| --- | --- | --- |
| 2 | Fascial chord tension medium = | Fascial groove to be added to selected design |
| 3 | Fascial chord tension high = | Deeper fascial groove to be added to selected design |

(3) Sagittal Plane Morphology Test

Figure 6:
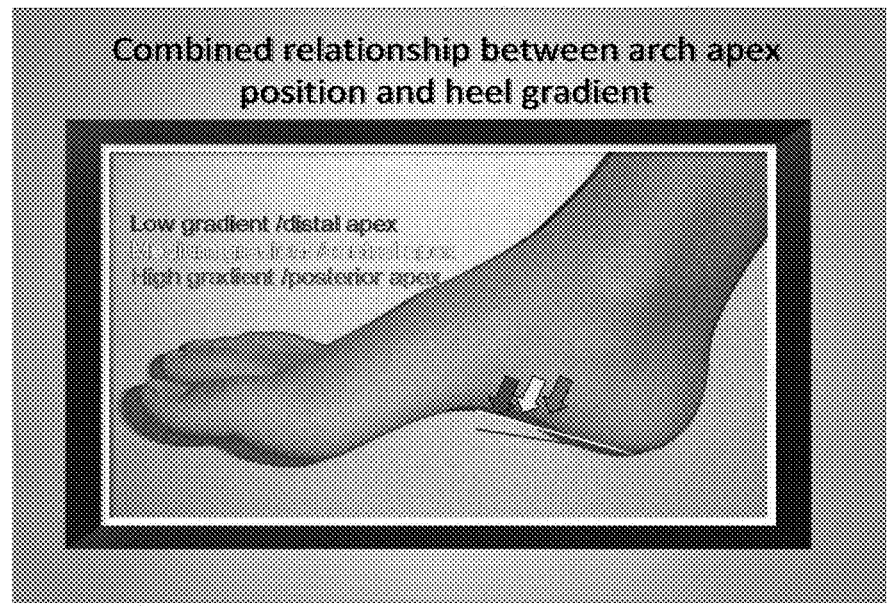
FIG. 6 illustrates the measurement of sagittal plane morphology in accordance with a representative embodiment of the present invention.

The Sagittal plane morphology of the foot (in medial aspect) is described with reference to both the gradient and foot apex position. The area over which the gradient applies is just anterior to the medial aspect of the Calcaneus and is evaluated low, medium, or high as shown in Table 8 below. The foot apex position (as demonstrated in FIG. 6 of the drawings) when combined with the gradient is categorised in terms of rear, central, and forward. This gives key information on the amount of soft tissue that surrounds the anterior area of the heel and which will determine rear foot correction applied. The design of certain orthotic designs is discussed later in this specification.

TABLE 8

| 1 | Anterior Apex/Low Gradient = | Extended heel |
| --- | --- | --- |
| 2 | Central Apex/Medium Gradient = | Kinetic control/Kinetic shell |
| 3 | Posterior Apex/high Gradient = | Kinetic rear control/Kinetic Blake |

(4) Hamstrings Tension Test

A test is done indicating the amount of tension in the hamstrings and so as to determine the possible compensatory impact on the ankle joint in the close kinetic chain. Hamstring tension is graded on three levels low, medium and high. When the tension is categorised as high changes are made to the design so as to facilitate sagittal plane function.

(5) Ankle Joint Stiffness-Lunge Test.

Figure 7:
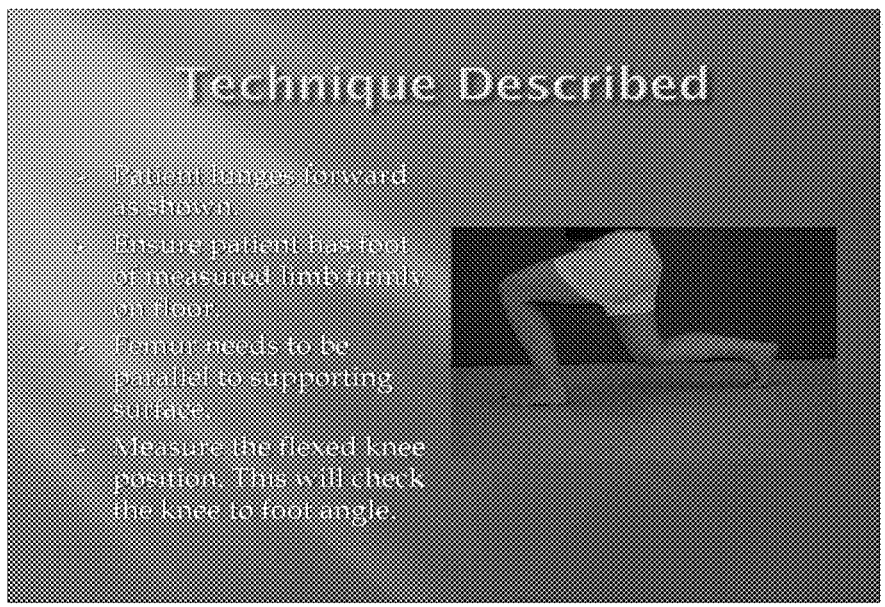
FIG. 7 illustrates the performance of a Lunge test in accordance with a representative embodiment of the present invention.

Ankle Joint stiffness is determined by the Lunge Test, as shown in FIG. 7 of the drawings and Table 9 below. When this test has failed, the degree of ankle joint facilitation is automatically increased in the design parameter. The design may also need to reflect the increasing force needed to establish foot resupination. As a result, the centre of pressure in the orthotic can shift further towards the rear. The design can be thus modified to provide the force necessary for foot resupination.

If the flexed knee position is 25-30°, this is considered to be a pass.

If the test is below 25°, then this is considered a fail.

Therefore it is possible to determine if there is a sagittal plane restriction that needs to be factored into the device.

Intra-rater and inter-rater reliability of a weight bearing lunge measure of ankle dorsiflexion. Bennett, K, Talbot, R, Wajswelner, H, Techovanich, W, Kelly, D. 1998. *Australian Physiotherapy*. Vol 44 (3) Pgs 175-181.

TABLE 9

| 1 | Pass lunge test = | No change to selected design |
| --- | --- | --- |
| 2 | Fail lunge test = | An increase in selected design correction and the further to the rear the correction needs to be applied in the design. |

(6) Principle Activity Velocity

This information when applied to the design is important because it can dictate whether we need to closely contour to the foot morphology or wedge the rear foot area of the orthotic. The rationale behind how this variable affects design is that the greater the velocity of the motion the greater is the force being transmitted to the orthotic device. In order to balance the increasing force at higher velocities it is necessary to adjust the design so as to concentrate the corrective forces further back in the orthotic.

At lower velocity where forces are low to moderate to begin with, the device can be contoured more closely to the morphology of the foot in order to spread the corrective support over a greater surface area (pressure equals force divided by area). For a given corrective force, the local pressure experienced will then be reduced.

1. low principal velocity=contoured design selected 2. medium principle velocity=contoured design with increased rear foot control 3. high principle velocity=rear controlling design selected regardless of initial contour

Non-Limiting Examples of the Invention

Design Criteria

Any specific orthotic design requires the combination of all the above factors.

By way of example, the core elements in kinetic orthotic design may grouped into six core design subgroups. Obviously more than six core designs may be used. However, solely for the purpose of the following illustration six key types of design are presented here. The six core designs described here are Kinetic Control, Kinetic Rear Control, Kinetic Shell, Kinetic Blake, Kinetic Extended Heel, and Kinetic Wedge.

Sample protocols for recording test results to be processed for orthotic design selection are set out below. The key variables are entered, as shown in FIGS. 9, 11, 13, 15, 17, and 19 of the drawings, and the design parameters are then applied to the manufacture of an orthotic according to the individual foot type.

Figure 8:
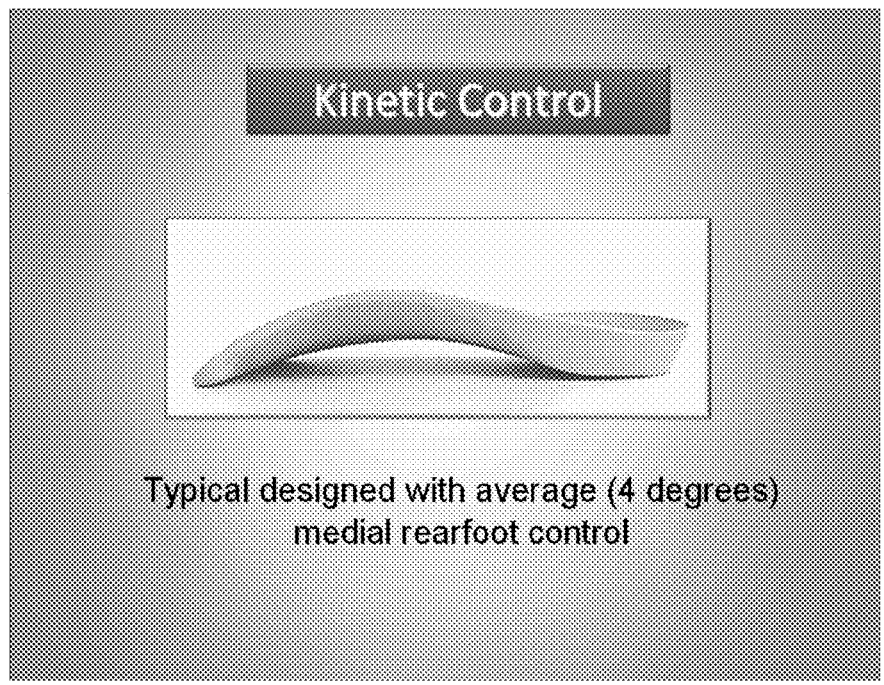
FIG. 8 illustrates a Kinetic Control orthotic design in accordance with a representative embodiment of the present invention.
Figure 9:
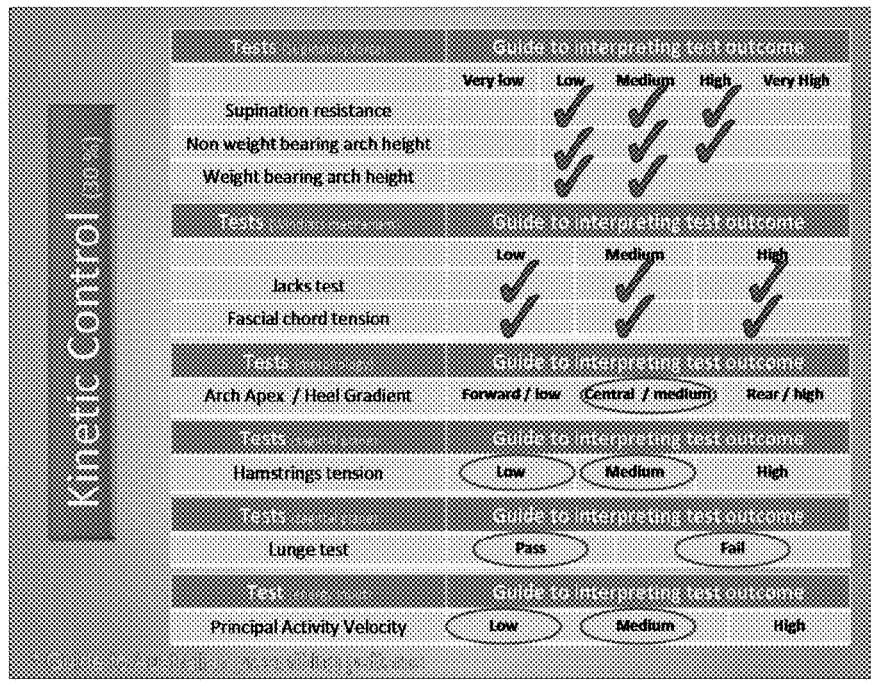
FIG. 9 illustrates test results for which the Kinetic Control orthotic design of FIG. 8 would be suitable.

(a) The Kinetic Control design, as shown in FIG. 8 of the drawings (and based on the variables shown in FIG. 9), has been developed following the established principals and incorporating many features of the modified Root approach to orthotic design.

Figure 10:
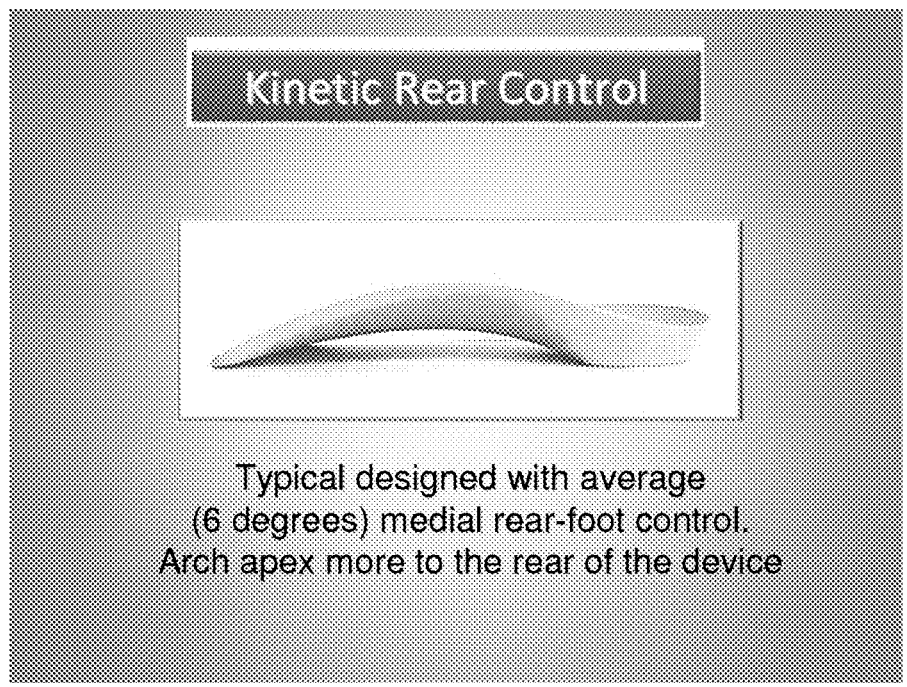
FIG. 10 illustrates a Kinetic Rear Control orthotic design in accordance with a representative embodiment of the present invention.

(b) The Kinetic Rear Control design, as shown in FIG. 10 of the drawings (and based on the variables shown in FIG. 11), as traditionally prescribed is similar to a heavily skived modified Root design such that the centre of pressure is shifted further to the rear of the orthotic thus essentially causing the apex to occur behind the navicular and more corrective pressure to be applied to the area below and around the sustimticulum-tali.

Figure 11:
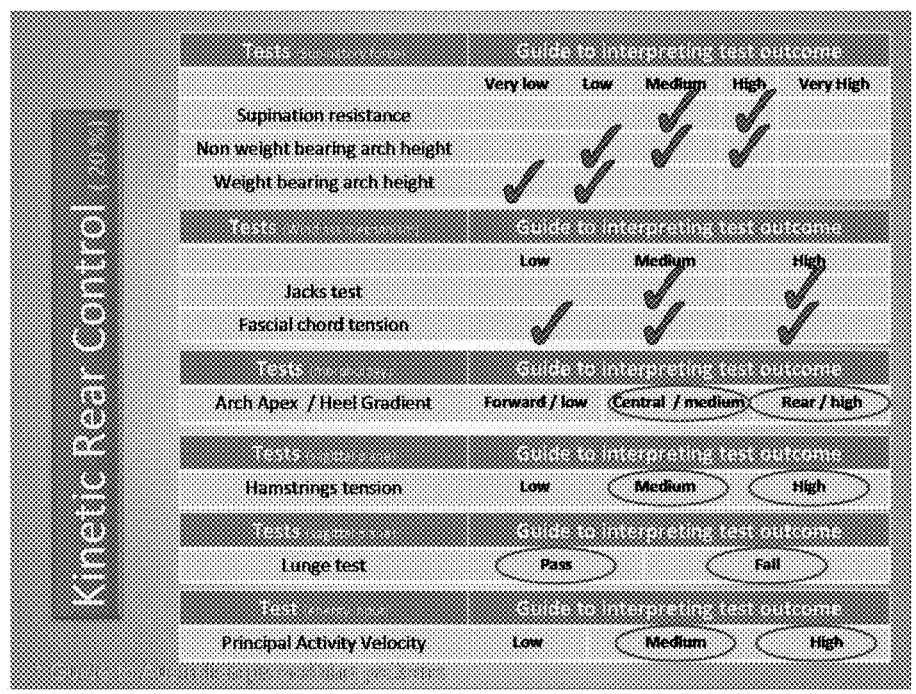
FIG. 11 illustrates test results for which the Kinetic Rear Control orthotic design of FIG. 10 would be suitable.

The table shown in FIG. 11 of the drawings outlines how the test parameters influence the premise of the design selection for the Kinetic Rear Control design. Again the lunge test and hamstring tension parameters critically influence the amount of heel elevation to be added to the design selected.

Figure 12:
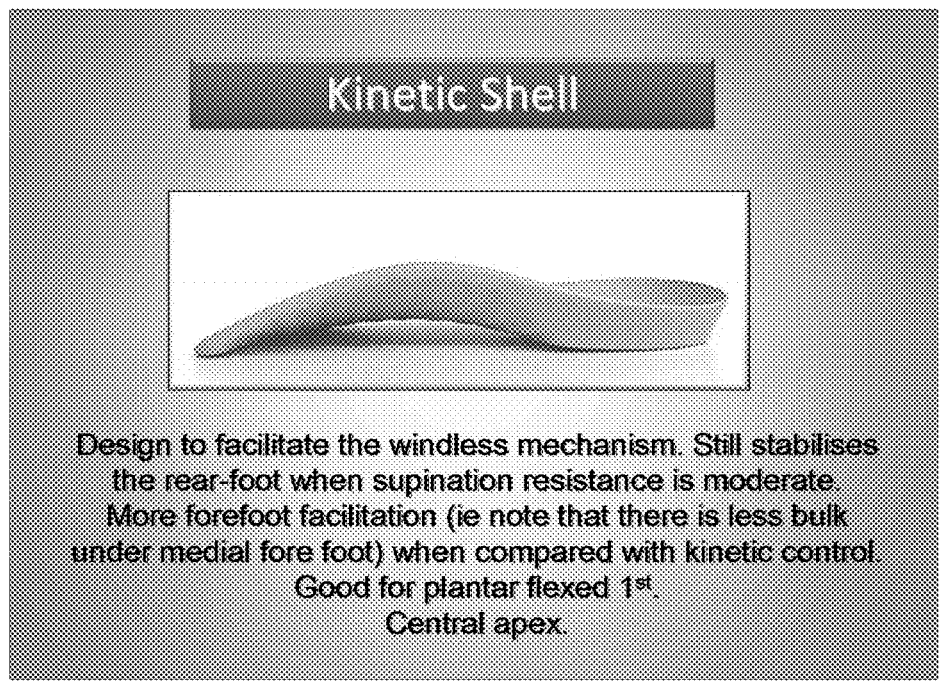
FIG. 12 illustrates a Kinetic Shell orthotic design in accordance with a representative embodiment of the present invention.
Figure 13:
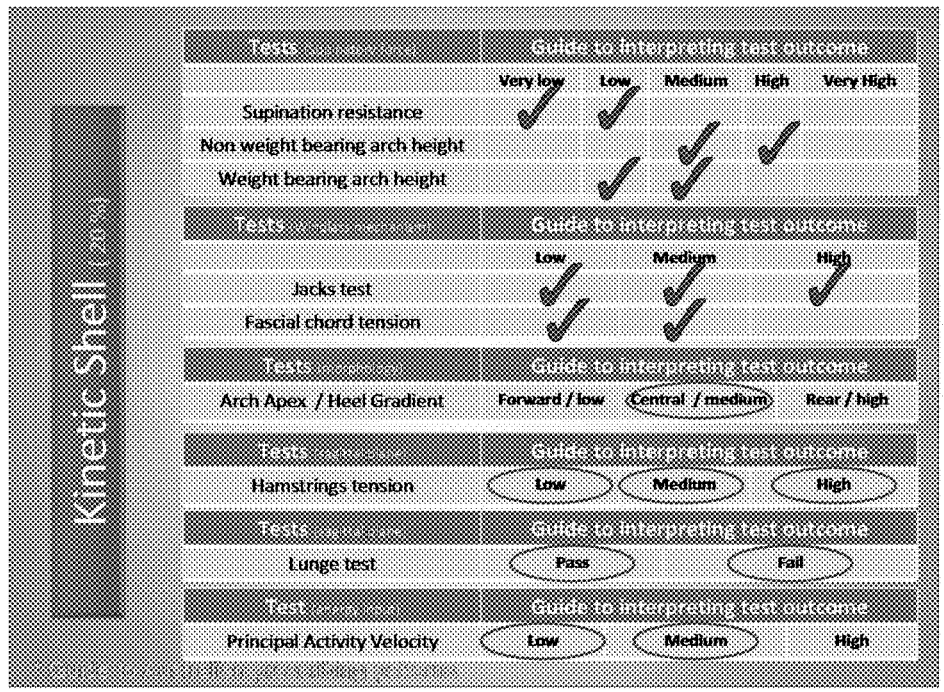
FIG. 13 illustrates test results for which the Kinetic Shell orthotic design of FIG. 12 would be suitable.

(c) The Kinetic Shell, as shown in FIG. 12 of the drawings (and based on the variables shown in FIG. 13), has been developed as a variation the modified Root style where support is applied via a subtle combination of rear foot and mid-foot control. It was designed so as to help facilitate sagittal plane function in feet where supination resistance was mild to moderate.

Figure 14:
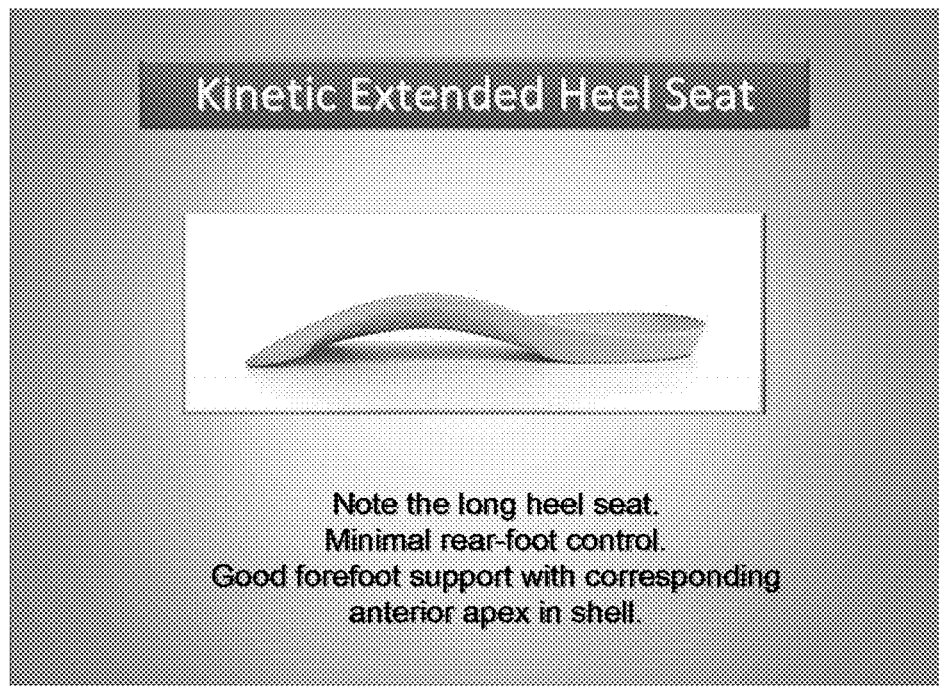
FIG. 14 illustrates a Kinetic Extended Heel orthotic design in accordance with a representative embodiment of the present invention.
Figure 15:
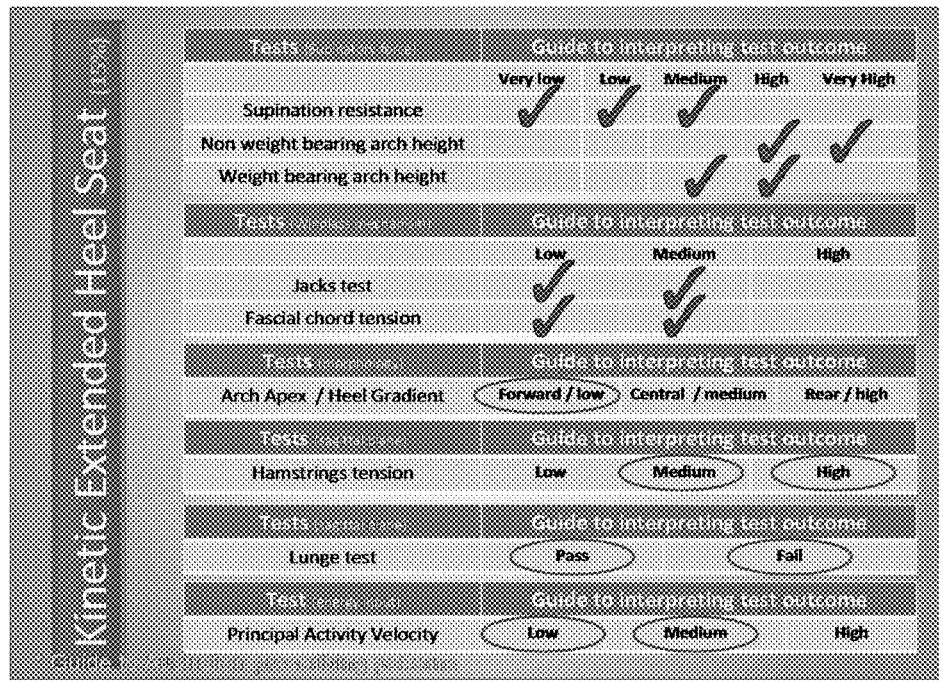
FIG. 15 illustrates test results for which the Kinetic Extended Heel orthotic design of FIG. 14 would be suitable.

(d) The Kinetic Extended Heel design, as shown in FIG. 14 of the drawings (and based on the variables shown in FIG. 15), characteristically provides little support to the rear foot area and greater support in the mid and fore-foot areas.

Figure 16:
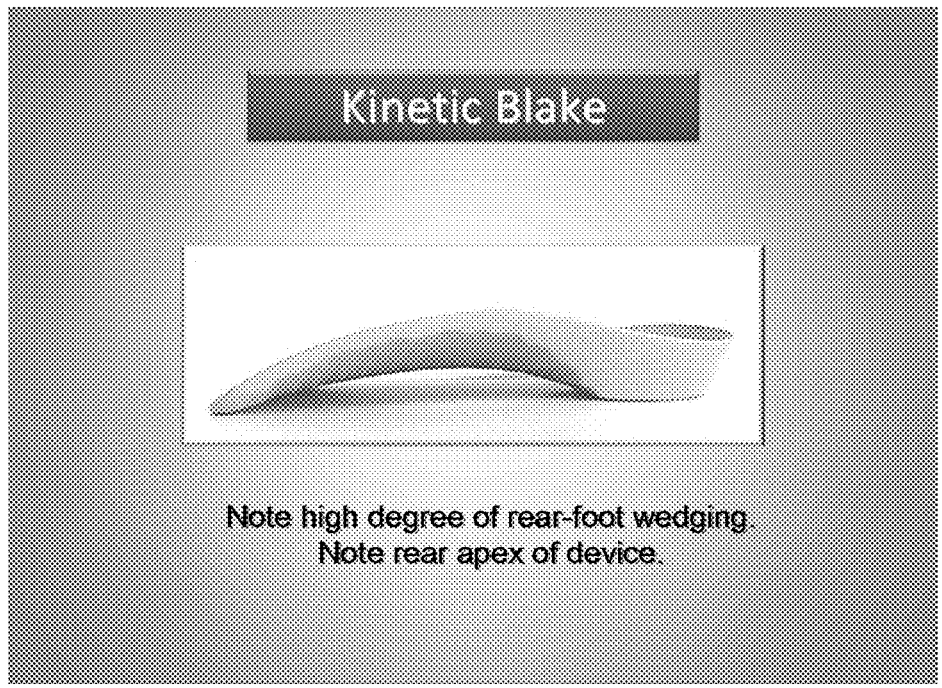
FIG. 16 illustrates a Kinetic Blake orthotic design in accordance with a representative embodiment of the present invention.
Figure 17:
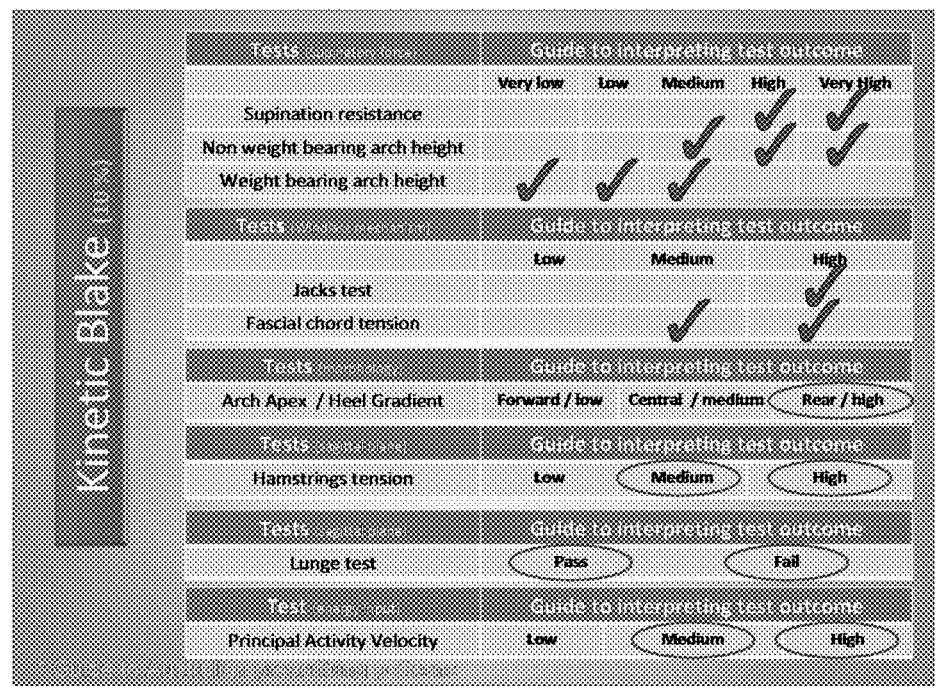
FIG. 17 illustrates test results for which the Kinetic Blake orthotic design of FIG. 16 would be suitable.

(e) The Kinetic Blake design, as shown in FIG. 16 of the drawings (and based on the variables shown in FIG. 17), has been developed along lines similar to a standard modified Blake device. This design uses rear foot wedging and skives for supporting the lateral column and cuboids.

Figure 18:
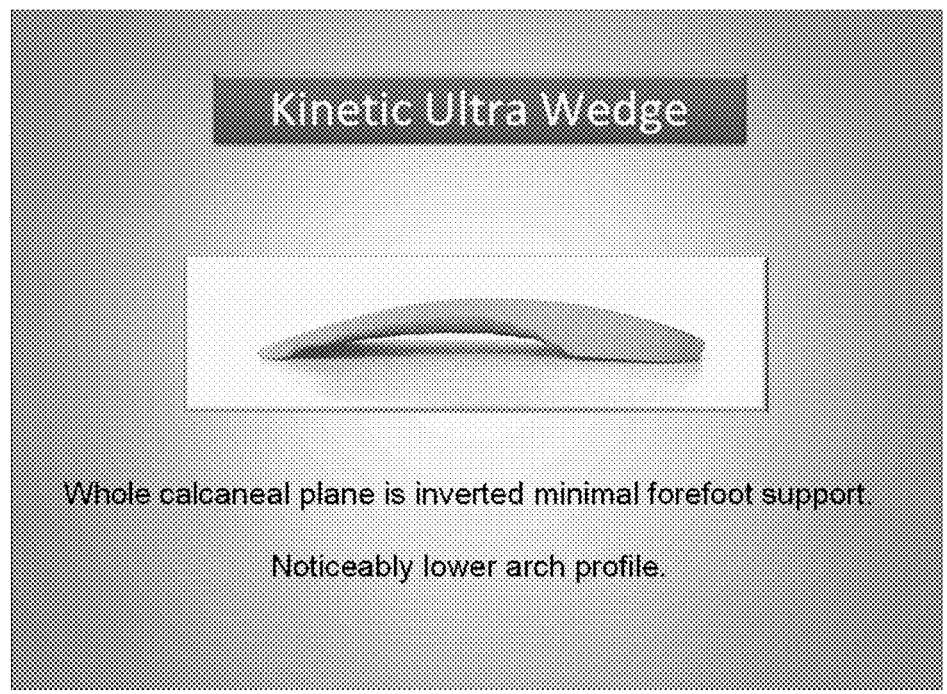
FIG. 18 illustrates a Kinetic Ultra Wedge orthotic design in accordance with a representative embodiment of the present invention.
Figure 19:
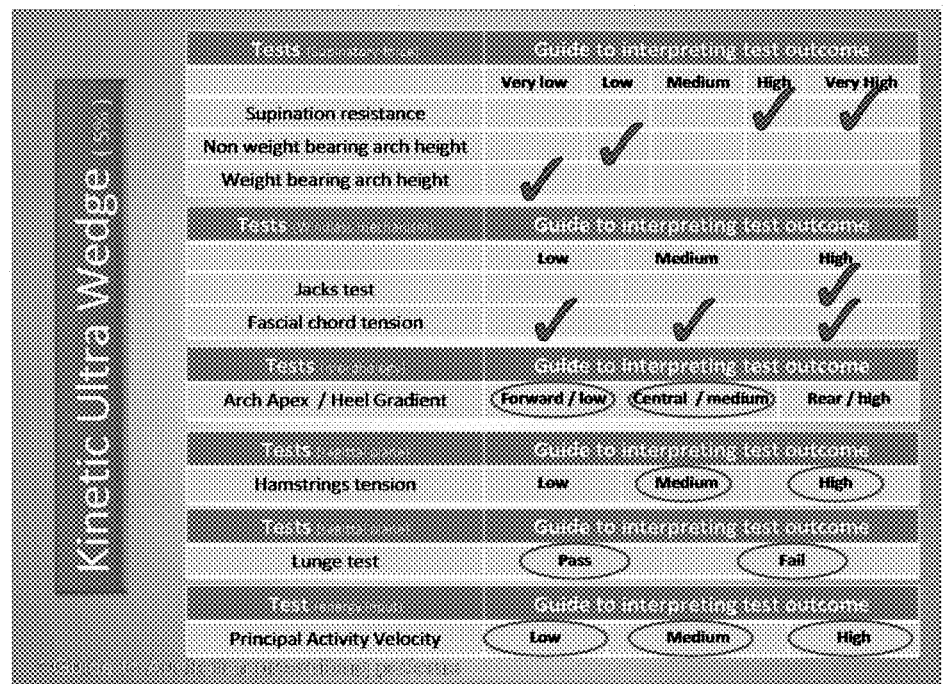
FIG. 19 illustrates test results for which the Kinetic Ultra Wedge orthotic design of FIG. 18 would be suitable.

(f) The Kinetic Ultra Wedge design, as shown in FIG. 18 of the drawings (and based on the variables shown in FIG. 19), applies corrective force via extreme rear foot wedging. Lateral column support is incorporated.

It is important to realize that different design styles are matched to differing foot morphology and differing requirements for rear foot wedging and positional apex pressure in the orthotic. How the design formats are to be used in applying support and facilitation is clearly indicated by the tables shown in FIGS. 9, 11, 13, 15, 17, and 19 of the drawings. The governing law should always be observed, namely that the relationship between stabilisation and facilitation of movement is intrinsic to how the anatomy of the foot is related to its physiology (for example hamstring tension and Lunge Test data influence the amount of extra heel elevation to be added to the original design, and fascial chord data also apply individually to the original design).

Supination resistance assessed by either test described above, is fundamental and affects the level of correction in two ways. Firstly the higher the supination resistance (or stiffness in Jacks Test) the further back must be the apex of curvature of the arch in the orthotic. Secondly: the higher the supination resistance (or resistance in Jacks Test) the greater the degree of correction that should be applied to the orthotic design.

Jacks test provides further information affecting the level of correction in two ways, via assessment of the arch apex/heel gradient (foot morphology) and the state of the Windlass Mechanism. The results affect the core design by indicating the area in which the starting apex position is to be applied. If the apex is to the rear with a high gradient, a design with a rear apex is chosen. If the apex is forward with a low gradient, a forward apex design is then selected. If the apex is central with a moderate gradient, then a central-apex design is selected.

The word 'comprising' and forms of the word 'comprising' as used in this description and in the claims does not limit the invention claimed to exclude any variants or additions.

In this specification, including the background section, where a document, act or item of knowledge is referred to or discussed, this reference or discussion is not an admission that the document, act or item of knowledge or any combination thereof was at the priority date, publicly available, known to the public, part of common general knowledge, or known to be relevant to an attempt to solve any problem with which this specification is concerned.

Modifications and improvements to the invention will be readily apparent to those skilled in the art. Such modifications and improvements are intended to be within the scope of this invention.

The claims defining the invention are as follows:

1. A method of treating foot protonation for a patient with an orthotic, the method comprising:
    A) determining an orthotic design using the method of:
        (a) subjecting a foot of the patient to a plurality of the following tests:
            (i) one or more supination force tests; and
            (ii) one or more windlass mechanism tests;
        (b) recording a test result for each test, each test result being indicative of one or more properties of the patient's foot;
        (c) ascribing a test category from a set of predetermined categories for each test result, the predetermined categories being indicative of one or more properties of the patient's foot;
        (d) recording each test category in a database;
        (e) comparing the test categories to a set of predetermined control categories stored in the database, the control categories being indicative of one or more predetermined orthotic designs; and
        (f) selecting an orthotic design from the predetermined orthotic designs dependent on that comparison; and
    (B) administering an orthotic to the patient in dependence on selection of the orthotic design so as to facilitate dynamic function of the patient's foot, wherein the orthotic design facilitates dynamic function of the patient's foot at a pivot point in the patient's foot.

2. The method of claim 1 wherein step (a) further includes a skeletal integrity test.

3. The method of claim 1 wherein step (a) further includes a fascial chord tension test.

4. The method of claim 1 wherein step (a) further includes an ankle joint stiffness-lunge test.

5. The method of claim 1 wherein step (a) further includes a principal activity velocity test.

6. The method of claim 1 wherein step (a) further includes a sagittal plane morphology test.

7. The method of claim 1 wherein step (a) further includes a hamstring stiffness test.

8. The method of claim 1 wherein the comparison step (e) includes the initial step of modifying one or more of the test values algorithmically prior to the comparison based upon a predetermined relationship between each test result contribution to orthotic design.

* * * * *